United States Patent [19]
Anderson et al.

[11] Patent Number: 5,197,491
[45] Date of Patent: Mar. 30, 1993

[54] ESOPHAGEAL-STOMACH DISPLACEMENT ELECTRODE

[75] Inventors: John Anderson, Holywood, Ireland; Carl E. Hewson, Marshfield, Mass.; David Cochran, Lisburn, Ireland

[73] Assignee: Brunswick Biomedical Technologies, Inc., Wareham, Mass.

[21] Appl. No.: 654,227

[22] Filed: Feb. 12, 1991

Related U.S. Application Data

[63] Continuation of Ser. No. 589,995, Sep. 28, 1990.

[51] Int. Cl.⁵ ............................................. A61N 1/05
[52] U.S. Cl. ..................................... 128/786; 128/642
[58] Field of Search ............... 128/696, 698, 639, 642, 128/733, 772, 774, 780, 8, 786, 784

[56] References Cited

U.S. PATENT DOCUMENTS

| | | | |
|---|---|---|---|
| 2,022,065 | 11/1935 | Wappler | 128/786 |
| 2,729,211 | 1/1956 | Peter | 128/780 |
| 3,516,412 | 6/1970 | Ackerman | 128/786 |
| 4,304,239 | 12/1981 | Perlin | 128/786 |
| 4,351,330 | 9/1982 | Scarberry | 128/786 |
| 4,706,688 | 11/1987 | Don Michnel et al. | 128/419 D |
| 4,920,980 | 5/1990 | Jackowski | 128/786 |

FOREIGN PATENT DOCUMENTS 1364350  1/1988  U.S.S.R. .................................. 128/8

Primary Examiner—Kyle L. Howell
Assistant Examiner—Kennedy J. Schaetzle
Attorney, Agent, or Firm—Wolf, Greenfield, Sacks

[57] ABSTRACT

An esophageal-stomach displacement electrode comprises a flexible tubular member designed to be inserted through the esophagus into the stomach. An electrode is carried by the tube in the region of its distal end. The tube is hinged near the distal end which enables that end of the tube to displace angularly in the stomach and displace the stomach wall. The stomach wall displacement may occur by angularly displacing the distal end or by otherwise pulling the tube partially out of the esophagus after its distal end partially displaced toward the stomach wall. A displacement mechanism is disposed in the tube in the region of the hinge and is controlled from a point externally of the body for causing the distal end of the tube to displace angularly, and to be positioned to engage and displace the stomach.

19 Claims, 5 Drawing Sheets

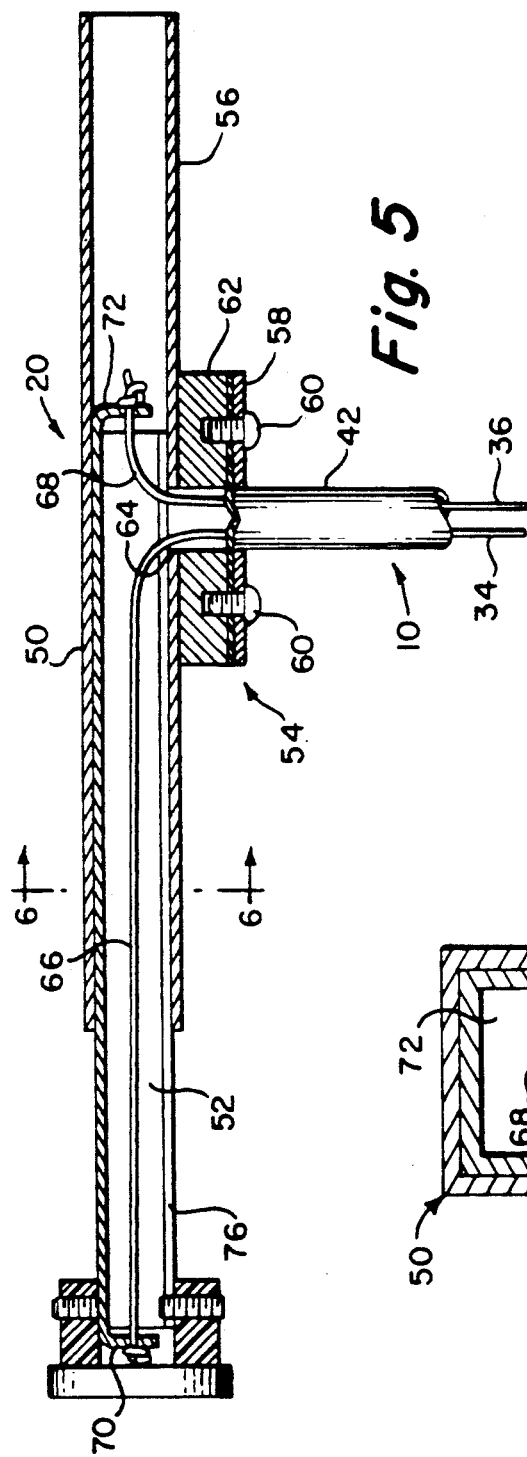
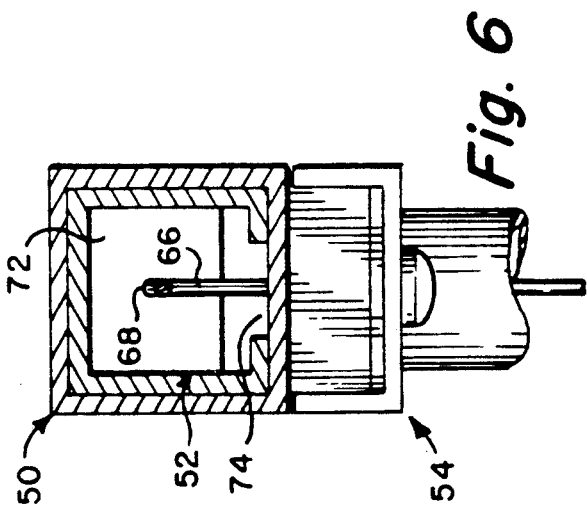

ESOPHAGEAL-STOMACH DISPLACEMENT ELECTRODE

PRIOR APPLICATION

This application is a continuation-in-part of my prior copending application Ser. No. 07/589,995 filed Sep. 28, 1990 entitled ESOPHAGEAL DISPLACEMENT ELECTRODE. That application is incorporated by reference herein.

FIELD OF THE INVENTION

This invention relates to esophageal electrodes and, more particularly, comprises such an electrode that may be inserted down a patient's esophagus and into the stomach with a portion of the electrode in contact with the stomach wall in a position most favorable for electrically stimulating the ventricle of the heart in cooperation with an external electrode placed on the patient's chest.

There are a number of medical procedures in which esophageal electrodes are used for such purposes as defibrillating and pacing the heart as well as for stimulating breathing. Examples of the use of esophageal electrodes in such procedures are shown in several United States patents and pending applications including Nos. 4,574,807, 4,683,890, 4,735,206, and 4,960,133; and Ser. Nos. 421,807 filed Oct. 16, 1989; 214,778 filed Jul. 5, 1988; and 812,015 filed Dec. 23, 1985 (now abandoned). An esophageal electrode may also be used as an ECG pickup. Those patents and applications are herein incorporated by reference. Many of these procedures may be substantially enhanced and facilitated if the electrode is capable of being moved close to the organ of the body being treated such as the ventricles of the heart.

Frequently patient care in a hospital and emergency care outside a hospital require ventricular pacing. Customarily, this is an invasive procedure and must therefore be performed in a sterile atmosphere, and the procedure requires a considerable period of time to perform. Many of the patents and applications identified above disclose a method and apparatus employing an internal, noninvasive esophageal electrode in combination with an external chest electrode, which are much more convenient to use, more efficient in performing the intended function, and do not require the presence of a physician.

The techniques described in the above identified patents and applications relating to pacing and/or defibrillation may be made more efficient if the electrode is positioned as close to the ventricle of the heart as possible. The closer the electrode is to the ventricle, the less electrical energy is needed to perform the pacing or defibrillating functions, and the more confident the attendant may be that the current flow between the internal and external electrodes is along the desired path.

The prior application Ser. No. 07/589,995, supra is directed to an esophageal displacement electrode to achieve greater efficiency in the practice of such procedures. The device includes a semi rigid plastic tube that may be inserted either orally or nasally into the esophagus. The tube carries an electrode at its distal end and has a mechanism incorporated into it which enables the user to cause the distal end of the tube to bend and press against the wall of the esophagus. The mechanism is of sufficient strength to cause the esophagus to displace under the pushing force of the electrode. To enable the tube to bend readily under the action of the mechanism, the tube is crimped so as to define a hinge at the distal region of the tube. The mechanism for deflecting the distal end of the tube includes a rigid pin having a cord connected at each end and which is aligned generally parallel to the axis of the tube and positioned at the distal portion thereof in the vicinity of the hinge. One cord attached to the proximal end of the pin extends out the proximal end of the tube, while the other cord attached to the distal end of the pin extends through a port located distally of the hinge in the tube and reenters the tube through a second port proximal of the hinge and then extends out the proximal end of the tube. By pulling on the cord attached to the distal end of the pin, the pin may be positioned beyond the hinge adjacent the distal port, and continued pulling of the cord will cause the tube t bend at the hinge.

The present invention is directed to an esophageal-stomach electrode to achieve greater efficiency in the performance of such procedures. The closer an electrode is positioned to the heart, the less electrical power is needed to control the heart and more consistent control of the heart is achieved. In accordance with the present invention a thin semi rigid plastic tube with the electrode on the distal end similar to the tube in the 07/589,995 application is used, but of sufficient length to be passed down the esophagus into the stomach. A mechanism, also similar to that in the earlier application, is incorporated into the tube which enables the user to cause the last couple of inches of the distal end of the tube to bend back on itself approximately 135 degrees from its original position. The user then withdraws the electrode until the bent back section of the distal end impacts on the stomach wall and displaces the stomach wall toward the heart. This action places the electrode in its operative position closest to the ventricle of the heart so as to cooperate with an external electrode on the chest to impress a pulse upon the heart. The bent back section of the distal end also prohibits further withdrawal of the electrode.

This invention will be better understood and appreciated from the following detailed description of a preferred embodiment thereof, selected for purposes of illustration and shown in the accompanying drawings.

BRIEF DESCRIPTION OF THE FIGURES

FIG. 5 is a side view of the control mechanism for the electrode shown in FIGS. 1 4 and showing one of the positions for the control slide; and FIG. 6 is a cross-sectional view of the control mechanism taken along section line 6 6 in FIG. 5.

DETAILED DESCRIPTION OF THE INVENTION

Figure 1:
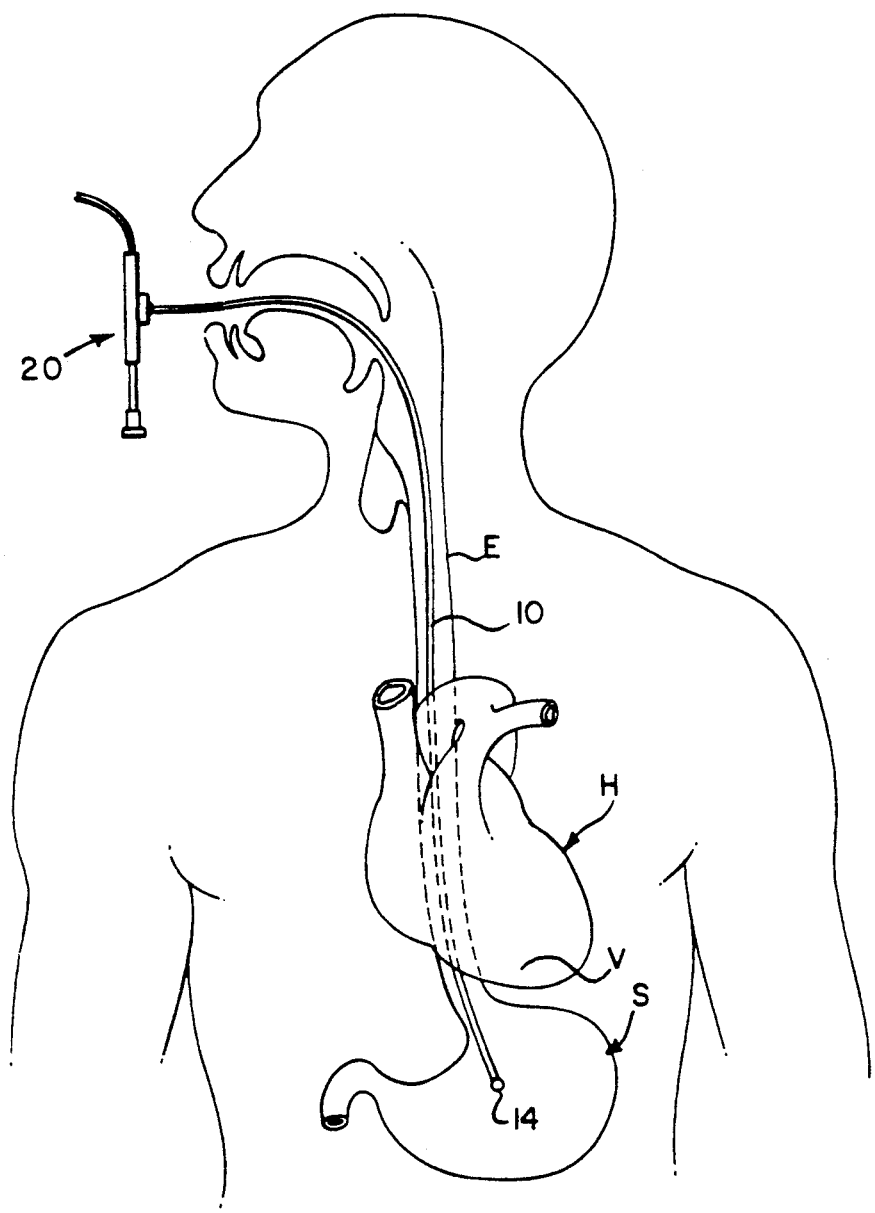
FIG. 1 is a diagrammatic frontview of a patient suggesting the heart, esophagus and stomach and showing without details of esophageal-stomach displacement electrode of the present invention extending through the esophagus and into the stomach.

In FIG. 1 the torso and head of a patient are shown along with the patient's heart H, esophagus E and stomach S. The stomach is located posterior and spaced from the ventricle V. The esophageal-stomach displacement electrode shown extends through the patient's mouth, through the esophagus and into the stomach with its distal end located relatively close to the ventricle V. The present invention enables the distal end of the esophageal-stomach displacement electrode to displace angularly within the stomach and subsequently be pulled slightly back out of the esophagus, or alternatively, further angularly displaced, upwardly into pressurized contact with the stomach wall to position the wall closer than normal to the heart (see FIG. 4) and thereby place the stomach displacement electrode in closer proximity to it. This is illustrated in FIGS. 2, and 3 and 4.

The electrode includes a semi rigid plastic tube 10 made of nylon or other suitable material which may be approximately 20 inches long and approximately 3/16 inch in diameter. The tube should be semi rigid, much like a gastric tube, and be relatively torque free. The distal end 12 of the tube carries an electrode 14, preferably spherical in shape and having a stem 16 that fits within the distal end of the tube. The electrode may be pressed in place or suitably fastened by other means. In the preferred form, the electrode 14 is ¼ inch in diameter, which just exceeds the diameter of the tube 10 so that the ball will make positive contact with the stomach wall when the distal end 12 of the tube 10 is displaced. The distal end 12 may be then further displaced or the complete electrode pulled back out of the esophagus to cause a bulge 50 (FIG. 4) in the stomach wall to place the wall and the electrode 14 closer to heart ventricle V. At this point, the electrode is prevented from further displacement by resistance of the stomach wall.

Figure 4:
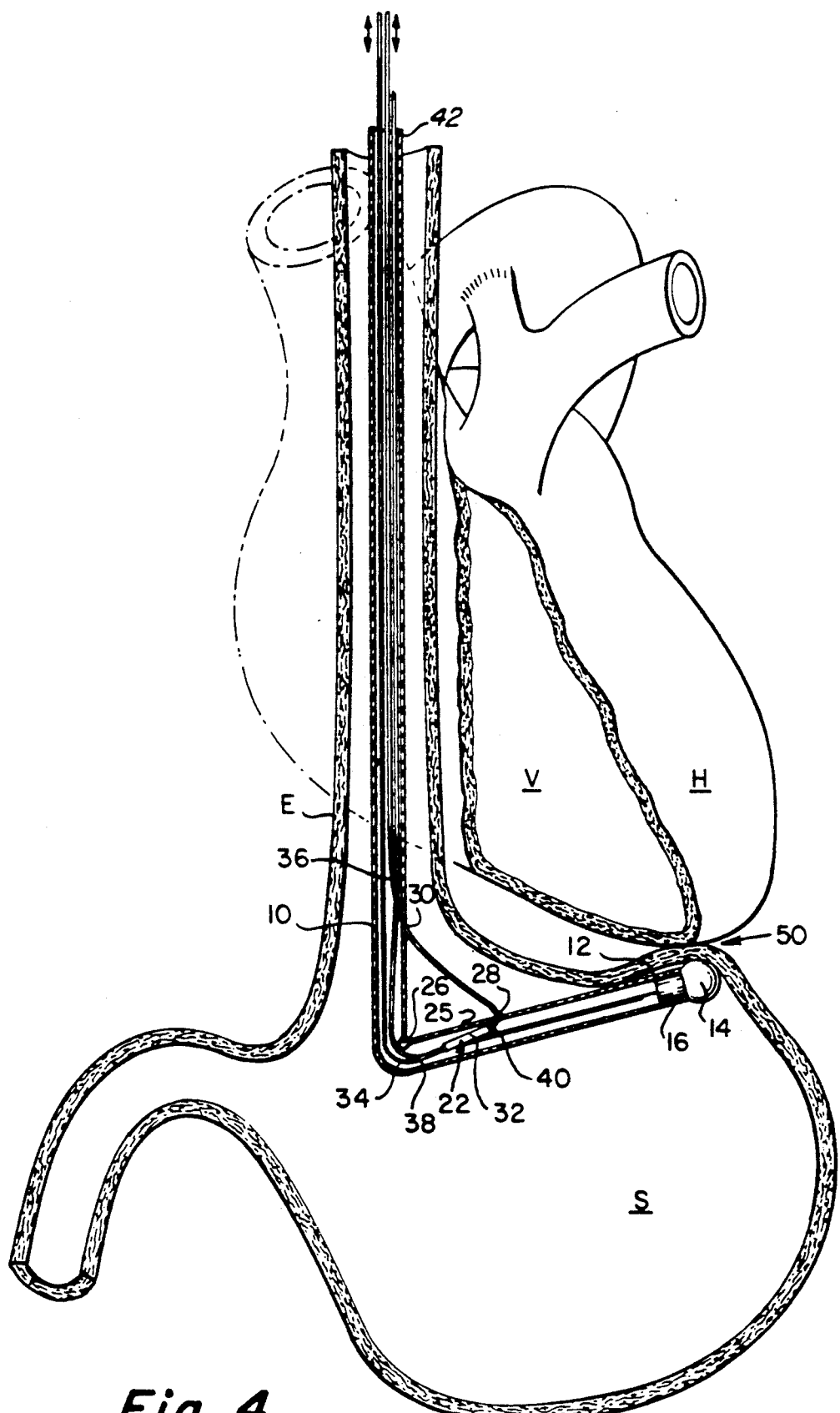
FIG. 4 is a view similar to FIG. 3 and showing the electrode elevated so that its tip engages the wall of the stomach and displaces the wall so that it essentially engages the heart.

The tube 10 is carried by a control mechanism 20 shown in FIG. 4 which is connected to a displacement mechanism 22 disposed in the tube. The control mechanism is located at the proximal end of the tube outside the mouth when the esophageal-stomach displacement electrode is placed in the stomach as shown in FIG. 1.

Figure 2:
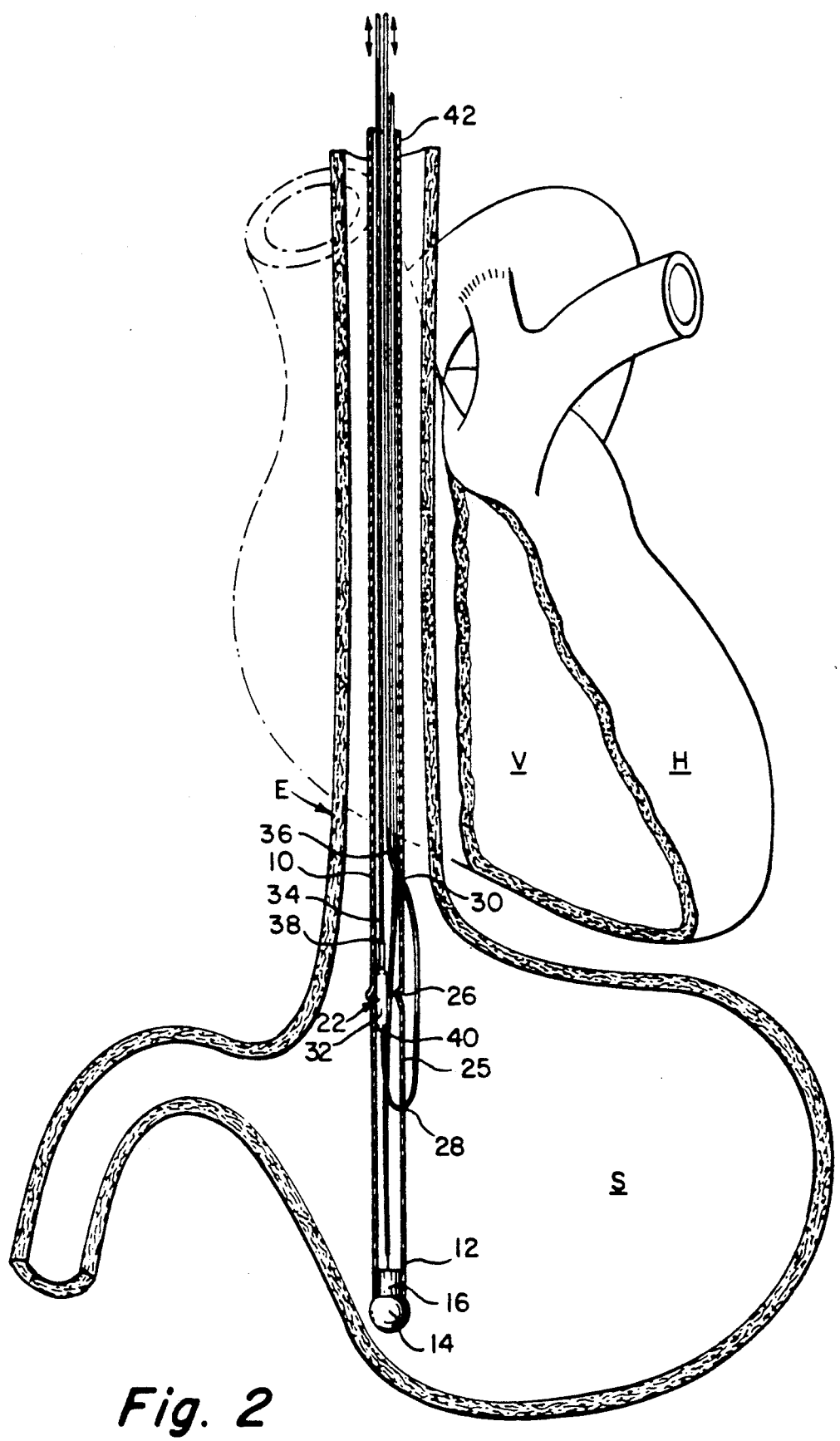
FIG. 2 is an enlarged cross-sectional view of the distal end of displacement electrode disposed in the stomach and with the distal end in the undisplaced position.
Figure 3:
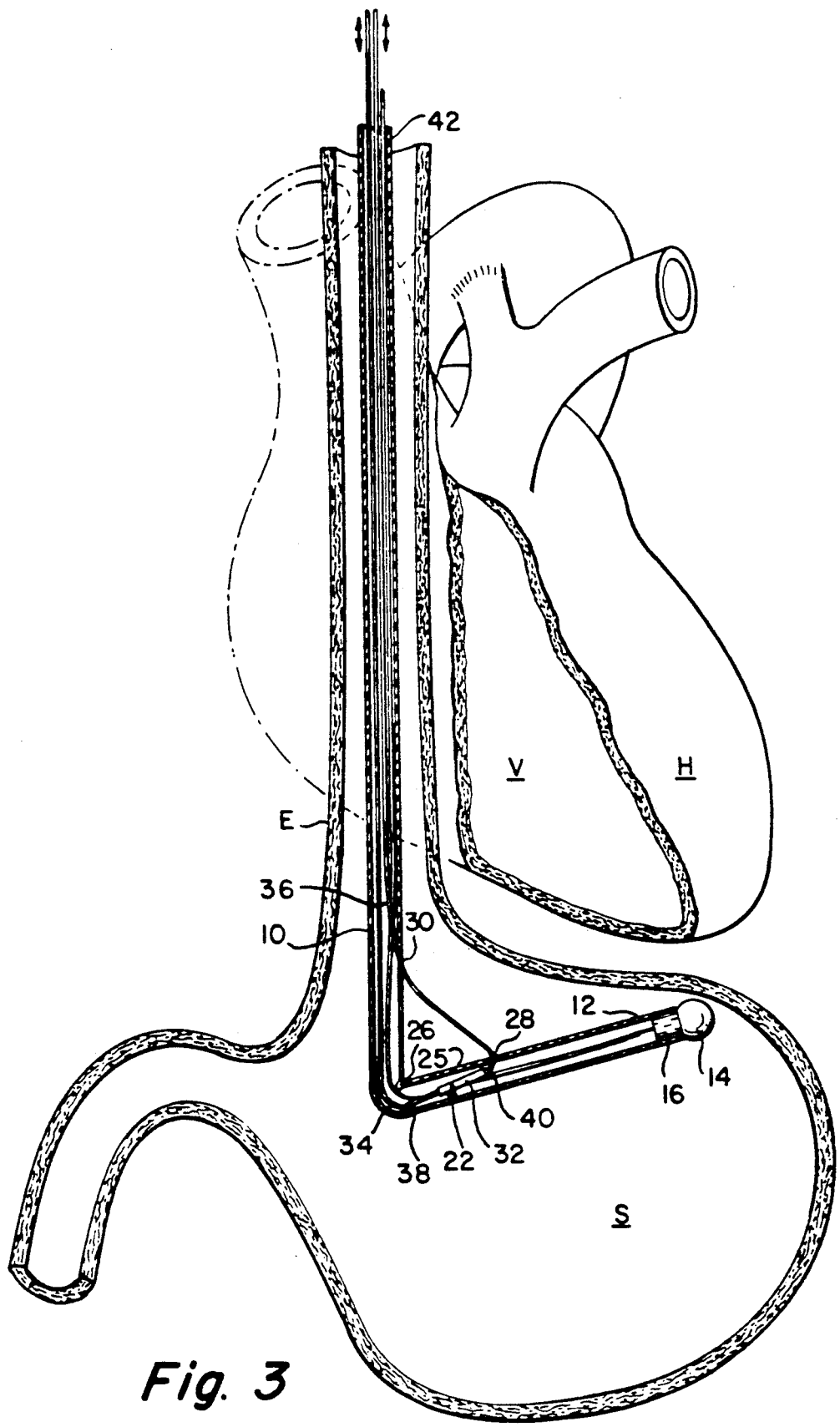
FIG. 3 is a view similar to FIG. 2 but showing the distal end of the electrode in its displaced position.

The tube 10 is crimped as suggested at 26 in FIGS. 2, 3 and 4 so as to form a hinge 27 in the tube, which enables it to bend readily at that point. In the wall 25 of the tube 10, ports 28 and 30 are formed on opposite sides of the hinge 27, each spaced approximately an inch therefrom. While in the embodiment shown, each of the two ports is approximately one inch from the crimp 26, that dimension as well as others given may be varied to suit the particular application, as is more fully described below.

A rigid pin 32 is disposed in the tube 10 and extends generally parallel to the tube axis. The pin may be made of metal, rigid plastic, or any other material having sufficient rigidity to prevent the tube 10 from bending at the crimped area 26 when the pin spans the hinge.

A pair of cords 34 and 36 are connected to the proximal and distal ends 38 and 40, respectively, of pin 32 and extend proximally in the tube 10 out its proximal end 42 and into the control mechanism 20. Cord 34 extends directly from the proximal end of the pin 32 within the tube 10 to the control mechanism 20, while cord 36 extends from the distal end 40 of the pin, out the tube 10 through port 28 and from that point it extends proximally externally of the tube, spanning the crimped portion 26 to the port 30 where the cord reenters the tube 10 and extends in the tube to the control mechanism 20. As is evident from FIGS. 2, 3 and 4, the location of the pin 32 may readily be changed by pulling one or the other of the cords 34 or 36 in a proximal direction.

Pin 32 is somewhat shorter than the distance between the crimped portion 26 of the tube and the lower port 28. Travel of the pin 32 in the tube 10 in a distal direction is limited by the location of port 28. The size of pin 32 is such that it cannot be drawn through port 28 and, therefore, when the pin 32 reaches its lowermost point and a continued pull is exerted on cord 36, the distal portion of the tube 10 is caused to deflect (in this example approximately 135°) from the position shown in FIG. 2 to that shown in FIG. 3. At this point the tube must still be further deflected or pulled back out of the stomach to place it into pressurized contact with the stomach wall to cause a bulge 50 as shown in FIG. 4. While the tube 10 is displaced or bent about the hinge 27 by pulling on cord 36 when pin 32 has reached its lowermost position, merely by releasing tension on the cord 36, the natural bias of the tube 10 to the configuration of FIGS. 1 and 2 will cause it to return to the shape shown therein.

The control mechanism 20 shown in FIG. 5 is connected to the distal ends of the cords 34 and 36 to operate the displacement mechanism 22 by taking up one cord and playing out the other. The control mechanism 20 includes a sleeve 50, rectangular in cross section in the embodiment shown, and containing a slide 52. A bracket 54 is secured to the bottom wall 56 of sleeve 50 and retains the proximal end 42 of tube 10 in place. The bracket 54 includes a bar 62 and clamping plate 58 that sandwich the tube end, and the plate 58 is secured to the bar 62 by screws 60.

The cords 34 and 36 enter the sleeve 50 through a port 64 in bottom wall 56, aligned with the proximal end 42 of the tube 10 when the tube is secured to the bracket 54. The proximal ends 66 and 68 of the cords are respectively connected to flanges 70 and 72 carried by the slide 52. In FIG. 5, slide 52 is shown in the position that places the pin 32 in the tube in the position shown in FIG. 2. When the slide is moved to the right as viewed in FIG. 5, the pin 32 moves to its lowermost position in tube 10 and the tube is deflected, as shown in FIG. 3. Because the slide 52 is generally U shaped with an opening 74 in its bottom wall 76 that rests upon the bottom wall 56 of sleeve 50, movement of the slide 52 in the sleeve 50 does not in any way interfere with the movement of the cords 34 and 36 in response to displacement of the slide.

The electrode typically may be used in the following manner. Assume that the electrode is part of a pacing mechanism as shown in U.S. Pat. No. 4,735,206, supra. The tube 10 is inserted into the esophagus either through the mouth or the nasal passage to a depth wherein the electrode 14 is disposed out the lower end of the esophagus into the stomach at a depth sufficient to enable displacement of the tube's distal end 12 to approximately 135 degrees from its straighten or insertion position as shown in FIG. 3. The external electrode also forming part of the pacer is mounted on the chest of the patient and the controls, etc. are properly set. In order to reduce the amount of electrical energy required to effect pacing, the operator moves the slide 52 to the right as shown in FIG. 5 which will cause the pin 32 to move downwardly in the tube 10 so that its distal end 40 is immediately adjacent the port 28. Further movement of the slide 52 in that direction will cause the distal portion of the tube 10 to deflect and place the electrode 14 in proximity to the upper stomach wall near the heart ventricle V., as shown in FIG. 3. Further deflecting the distal end 12 or pulling back the tube 10 at its proximal portion then places the electrode 14 in pressurized displacable contact with the upper stomach wall causing a bulge that places the electrode closer to the ventricle V (FIG. 4). With the electrode in the displaced position of FIG. 4, the pacing pulses are imposed across the electrodes. When the procedure is completed, the operator may move the slide 52 back to the position of FIG. 5, which will relieve the tension on the cord 36 and allow the tube 10 to return to the position of FIG. 2. Thereafter the tube 10 may be withdrawn.

From the foregoing description, those skilled in the art will appreciate that the present invention provides a very convenient means of enabling an operator to place the esophageal stomach displacement electrode very close to the heart or other organ by means of a noninvasive procedure and thereby reduce the energy required to carry out the particular procedure such as pacing or defibrillation upon the patient. It will also be appreciated that while a specific embodiment is shown in the drawings, modifications may be made thereof without departing from this invention. For example, while a pin is shown as applying the bending force to the interior of the tube, other configurations for the device may be employed. Any structure which will not pass through the lower port 28 and will not interfere with the action of the hinge 27 will cause the tube 10 to deflect when the cord attached to it and exiting the tube through the port 28 is tensioned. It should, if necessary, also stiffen the hinge portion of the tube when it is being inserted in the esophagus and stomach. The member which applies the bending force must be capable of moving freely in the tube under the operation of the control 20 so as to be readily movable in response to actuation of the control. The tube 10 could, of course, carry more than one electrode. For example, in the earlier patents, supra, a number of spaced contact rings are shown carried by the tube.

Because modifications may be made of the invention without departing from its spirit, it is not intended that the scope of this invention be limited to the specific embodiment illustrated and described. Rather, the scope of this invention is to be determined by the appended claims and their equivalents.

What is claimed is:

1. An esophageal-stomach displacement electrode comprising:
   a flexible hollow tube having proximal and distal ends adapted to be inserted through the esophagus into the stomach with the distal end extending to a region in the stomach proximate the ventricles of the heart and the proximal end disposed externally of the body;
   an electrode carried by the tube at its distal end;
   means in the tube enabling the distal end thereof to displace laterally with respect to the tube axis so as to be disposed proximate the wall of the stomach near the ventricles so that longitudinal displacement of the tube in a proximal direction places the stomach wall immediately adjacent the ventricles, and enables the electrode carried by the tube at its distal end to lie closely adjacent the ventricles, the enabling means including a bendable section provided in the tube a short distance proximally of the distal end; and
   displacement means disposed in the tube and controlled by a control mechanism from a point externally of the body for causing the tube to place the stomach and the electrode nearer the heart wherein the control mechanism is located at the proximal end of the tube.

2. An esophageal-stomach displacement electrode as described in claim 1 wherein the displacement means includes means for resisting bending of the tube at the bendable section.

3. An esophageal-stomach displacement electrode as described in claim 1 wherein the displacement means includes a member disposed in the tube in the vicinity of the bendable section, the member having a diameter smaller than that of the tube enabling the member to move longitudinally within the tube including movement to an extreme distal position distally of the bendable section,
   and means attached to the member and operable from a location externally of the body for causing it to push against and deflect the portion of the tube distal to the bendable section so as to place the electrode closer to the stomach wall.

4. An esophageal-stomach displacement electrode as described in claim 3 wherein the means attached to the member includes a cord connected to the member, a distal and a proximal port in the tube disposed on opposite sides of the bendable section, said cord exiting the tube through the distal port and reentering the tube through the proximal port and extending through the tube to the control mechanism.

5. An esophageal stomach displacement electrode as described in claim 4 further comprising means for preventing the member from being drawn out the tube through the distal port.

6. An esophageal stomach displacement electrode as described in claim 5 wherein the control mechanism includes a sleeve and slide disposed in the sleeve and attached to the cord for pulling the cord so as to move the member to the extreme distal position and displace the portion of the tube distally of the bendable section.

7. An esophageal-stomach displacement electrode as described in claim 5 wherein a second cord is attached to the member and extends from the member proximally out of the tube to the control mechanism.

8. An esophageal-stomach displacement electrode as described in claim 7 wherein the control mechanism includes means attached to the cords for taking up one of the cords while playing out the other.

9. An esophageal-stomach displacement electrode as described in claim 8 wherein the control mechanism includes a sleeve and a slide movable in the sleeve for taking up and playing out the cords.

10. An esophageal-stomach displacement electrode comprising:
    a flexible hollow tube having proximal and distal ends adapted to be inserted through the esophagus into the stomach with the distal end extending to a region proximate the ventricles of the heart and the proximal end disposed externally of the body;
    an electrode carried by the tube at its distal end;
    means in the tube enabling the distal end thereof to displace laterally with respect to the tube axis so as to be disposed proximate the wall of the stomach near the ventricles so that sufficient axial displacement of the tube in a proximal direction places the stomach wall immediately adjacent the ventricles and the electrode closedly adjacent the ventricles;

and displacement means disposed in the tube and controlled from a point externally of the body for causing the distal end of the tube and the electrode to engage the stomach and place the electrode nearer the heart.

11. An esophageal-stomach displacement electrode as described in claim 1 wherein the displacement means includes a member having a diameter smaller than that of the tube enabling the member to move longitudinally within the tube including movement to a point below the first-named means and a cord connected to the member and extending out the proximal end of the tube.

12. An esophageal stomach displacement electrode as described in claim 11 wherein the member is a rigid pin extending longitudinally of the tube, and said cord spans the first named means externally of the tube.

13. An esophageal stomach displacement electrode as described in claim 12 wherein a pair of ports are provided in the tube, one on each side of the first named means, and said cord exits from the tube in the port distally of the first named means and reenters the tube through the other port and extends proximally therefrom in the tube to the proximal end of the tube.

14. An esophageal stomach displacement electrode as described in claim 10 wherein the first named means is a crimp in the tube causing it to bend at the crimp when the distal end of the tube is pulled proximally by the displacement means.

15. An esophageal-stomach displacement electrode comprising:

a flexible tubular member having proximal and distal ends adapted to be inserted through the esophagus into the stomach;

an electrode carried by the tube in the region of its distal end;

said tube having hinge means enabling the distal end of the tube to angularly displace in the stomach and contact and displace the stomach when the distal end of the tube is fully displaced;

and displacement means disposed in the tube and controlled from a point externally of the body for causing the distal end of the tube to angularly displace, and engage and displace the stomach when the distal end is fully angularly displaced.

16. A method of noninvasively placing an electrode in the body closely adjacent a selected body organ comprising the steps of:

inserting an elongated member carrying an electrode at its distal region through the esophagus into the stomach;

displacing the distal region of the elongated member in the stomach to place the electrode in contact with the stomach wall, and thereafter moving the elongated member in a proximal direction to place the stomach wall and electrode closely adjacent the selected organ.

17. The method as set forth in claim 16 wherein the step of displacing includes displacing the distal region at an angle in the range of 135° from an undisplaced position.

18. The method as set forth in claim 16 wherein the step of displacing includes the step of bending the distal region partially back upon itself.

19. The method as set forth in claim 18 wherein the step of bending the distal region includes the step of bending the distal region approximately 135° from its original position.

* * * * *